US008232264B2

(12) United States Patent
Gans et al.

(10) Patent No.: US 8,232,264 B2
(45) Date of Patent: *Jul. 31, 2012

(54) COMPOSITIONS AND METHODS FOR ENHANCING CORTICOSTEROID DELIVERY

(75) Inventors: Eugene H. Gans, Westport, CT (US); Mitchell S. Wortzman, Scottsdale, AZ (US)

(73) Assignee: Medicis Pharmaceutical Corporation, Scottsdale, AZ (US)

( * ) Notice: Subject to any disclaimer, the term of this patent is extended or adjusted under 35 U.S.C. 154(b) by 443 days.

This patent is subject to a terminal disclaimer.

(21) Appl. No.: 12/322,346

(22) Filed: Jan. 29, 2009

(65) Prior Publication Data

US 2009/0176750 A1 Jul. 9, 2009
US 2010/0210609 A2 Aug. 19, 2010

Related U.S. Application Data

(63) Continuation of application No. 10/825,977, filed on Apr. 16, 2004, now abandoned, which is a continuation of application No. 10/037,360, filed on Dec. 21, 2001, now Pat. No. 6,765,001.

(51) Int. Cl.
*A61K 31/58* (2006.01)
*A61K 31/56* (2006.01)
*A61K 47/00* (2006.01)
*A61K 9/00* (2006.01)

(52) U.S. Cl. ........ 514/172; 514/169; 514/170; 514/177; 514/178; 514/179; 514/180; 514/769; 424/400

(58) Field of Classification Search .................. 514/172, 514/169, 170, 177–180, 769; 424/400
See application file for complete search history.

(56) References Cited

U.S. PATENT DOCUMENTS

| | | | |
|---|---|---|---|
| 3,592,930 A | 7/1971 | Katz et al. | |
| 3,934,013 A | 1/1976 | Poulsen | |
| 4,017,615 A | 4/1977 | Shastri et al. | |
| 4,831,023 A | 5/1989 | Garlen et al. | |
| 4,855,294 A | 8/1989 | Patel et al. | |
| 4,879,119 A * | 11/1989 | Konno et al. | 424/449 |
| 5,662,890 A * | 9/1997 | Punto et al. | 424/59 |
| 6,075,056 A | 6/2000 | Quigley, Jr. et al. | |
| 6,300,326 B1 | 10/2001 | Dobbs et al. | |
| 6,765,001 B2 | 7/2004 | Gans et al. | |
| 2003/0232086 A1 | 12/2003 | McCadden | |
| 2004/0198709 A1 | 10/2004 | Gans et al. | |
| 2005/0192261 A1 | 9/2005 | Jost-Price et al. | |

FOREIGN PATENT DOCUMENTS

| | | |
|---|---|---|
| EP | 0 020 794 A | 1/1981 |
| EP | 0097374 A2 | 1/1984 |
| EP | 0793966 A1 | 9/1997 |
| JP | 58225009 A | 12/1983 |
| JP | 61036219 A | 2/1986 |
| JP | 63255228 A | 10/1988 |
| JP | 10007584 A | 1/1998 |
| JP | 10204001 A | 8/1998 |
| JP | 11158060 A | 6/1999 |
| WO | WO 91/08733 A | 6/1991 |

OTHER PUBLICATIONS

Hench, et al. "The Effect of a Hormone of the Adrenal Cortex (17-Hydroxy-11-Dehydrocorticosterone: Compound E) and of Pituitary Adrenocorticotropic Hormone on Rheumatoid Arthritis" Proceedings of the Staff Meetings of the Mayo Clinic (1949) col. 24, No. 8, pp. 182-197.
Fieser, et al. "Adrenocortical Hormones" Steroids (1950) Chapter 19, pp. 600-610.
Hench, et al. "Cortisone—Its Effects of Rheumatoid Arthritis, Rheumatic Fever, and Certain Other Conditions" The Merck Report (1950) pp. 9-14.
Wieland, et al. "Ester der Nebennierenrinden-Hormone mit Protrahierter Wirkung" (1951) pp. 354-358.
Sulzberger, et al. "The Effect of Topically Applied Compound F in selected Dermatoses" The Journal of Investigative Dermatology (1952) vol. 19, pp. 101-102.
Fried, et al. "The Use of Microorganisms in the Synthesis of Steroid Hormones and Hormones Analogues" Recent Progress in Hormone Research (1955) vol. XI, pp. 149-181.
Herzog, et al. "New Antiarthritic Steroids" Science (1955) vol. 121, p. 176.
Ringold, et al. "Steroids. LXXV. Dehydrogenation of Testosterone to $\Delta^{1,4}$-Androstadien-17β-o1-3-one with Selenium Dioxide" The Journal of Organic Chemistry (1956) vol. 21, No. 2, pp. 239-240.
Hogg, et al. "6-Fluoro Analogues of Steroid Hormones" Chemistry and Industry (1958), pp. 1002-1003.
Fried, et al. "Cyclic 16α, 17α-Ketals and Acetals of 9α-Fluoro-16A-Hydroxy-Cortisol and- Prednisolone" The Journal of the American Chemical Society (1958) vol. LXXX, pp. 2338-2339.
Bowers A., et al. Synthesis of halogenated steroid hormones—II, 6α- and 6β-fluorotestosterone and 6α- and 6β fluoroprogesterone. Tetrahedron The International Journal of Organic Chemistry (1958) 3, pp. 14-27. Bowers, et al. "Steroids, CIII. A new class of potent Cortical Hormones, 6α-Fluorocorticoids" The Journal of the American Chemical Society (1958), pp. 4423-4424.
Scholtz, J.R. "Topical Therapy of Psoriasis with Fluocinolone Acetonide" Archives Dermatology, (1961) vol. 84, pp. 191-192.
McKenzie, et al. "Method for Comparing Percutaneous Absorption of Steroids" Archives of Dermatology (1962) vol. 86, pp. 88-90.
Katz, et al. "Percutaneous Corticosteroid Absorption Correlated to Partition Coeffecient" Journal of Pharmaceutical Sciences (1965) vol. 54, No. 4, pp. 591-594.
Syntex: A Corporation and a Molecule: The Story of Research at Syntex (1966).
Place, et al. "Precise Evaluation of Topically Applied Corticosteroid Potency" Archives of Dermatology (1970) vol. 101, No. 5, pp. 531-537.
Katz, et al. "Absorption of Drugs through the Skin" Handbook of experimental Pharmacology (1971) vol. 28, Part 1, pp. 104-162.
Kendall, E.C. "Arthritis" Cortisone (1971), pp. 121-137.

(Continued)

*Primary Examiner* — Shengjun Wang

(74) *Attorney, Agent, or Firm* — William J. McNichol, Jr.; Maryellen Feehery Hank; Reed Smith LLP

(57) ABSTRACT

The present invention comprises a composition, method of enhancing potency and method of delivering corticosteroids in a vehicle comprising at least two penetration enhancers, and solvents and emulsifiers. The propylene glycol and penetration enhancers are present in ratio to the total of the propylene glycol, penetration enhancers, and solvents and emulsifiers of at least about 0.70.

56 Claims, No Drawings

OTHER PUBLICATIONS

Ostrenga, et al. "Vehicle Design for a new Topical Steroid, Fluodinonide" The Journal of Investigative Dermatology (1971) vol. 56, No. 5, pp. 392-399.

Reinstein, et al. "Design of the Optimal Topical System for Fluocinonide" Acta Dermato-Venereologica (1971) vol. 52, Suppl. 67, pp. 13-18.

Counce, et al. "Fluocinonide: A new Topical Corticosteroid for Psoriasis and other Dermatoses" The Journal of the Louisiana State Medical Society (1972) vol. 124, No. 10, pp. 365-367.

Dumas, et al. "The Psoriasis Bio-Assay for Topical Corticosteroid Activity" Acta Dermatovener (Stockholm) (1972) vol. 52, pp. 43-48.

Katz M., et al. "Corticoid, Vehicle, and Skin Interaction in Percutaneous Absorption" Journal of the Society of Cosmetic Chemists (1972) vol. 23, No. 9, pp. 565-590.

Haleblian J. "Bioassays Used in Development of Topical Dosage Forms" Journal of Pharmaceutical Sciences (1976) vol. 65, No. 10, pp. 1417-1436.

Wolff, M.E. "Structure-Activity Relationships in Glucocorticoids" Glucocorticoid Hormone Action (1979), Chapter 5, pp. 97-107.

Barry, B.W. "Dermatological Formulations" New York: Marcel Dekker, Inc. (1983) pp. 264-280.

Ponec, M. "Effects of Glucocorticoids on Cultured Skin Fibroblasts and Keratinocytes" International Journal of Dermatology (1984) vol. 23, No. 1, pp. 11-24.

Bennett et al., "Optimization of bioavailability of topical steroids: non-occluded penetration enhancers under thermodynamic control", Journal of Pharmacy and Pharmacology, vol. 37, No. 5, 1985, pp. 298-304.

Hollenberg, et al. "Primary Structure and Expression of a Functional Human Glucocorticoid Receptor cDNA" Nature International Weekly Journal of Science (1985) vol. 318, No. 6047, pp. 635-641.

Murray, J.R. "The History of Corticosteroids" Updates in Dermatology (1989) vol. 69, Suppl. 151, pp. 4-6.

Djerassi C. "The pill, pygmy chips, and Degas' Horse" New York: Basic Books (1992) pp. 34-48.

Stouch, T.R. Structure-Activity Relationships using Multivariate Analysis Techniques: Application to Topical Corticosteroids, Maibach HI, Surber C (1992) pp. 93-127.

Stoughton, R.B. "Vasoconstrictor Assay—Specific Applications" Topical Corticosteroids (1992), pp. 42-53.

Ponec M. "Glucocorticoid Receptors", Topical Glucocorticoids with Increased Benefit/Risk Ratio (1993) vol. 21, pp. 20-28.

Murphy W.B. "A Half Century of Innovation at Syntex" Science Serendipity (1994).

Mori, et al. "Topical Corticosteroids and Unwanted Local Effects," Drug Safety, 10 (5) 1994, p. 406-412.

Birch, A.J. "Profiles, Pathways and Dreams" To See the Obvious; American Chemical Society, Washington DC (1995), pp. 87-92.

Schafer-Korting, et al. "Topical Glucocorticoids with Improved Risk-Benefit Ratio," Drug Safety Jun. 1996; 14 (6), p. 375-385.

Dermatology in General Medicine, 5th ed. CD-ROM, 1999, Chapter 243, p. 1-10, Tables 243-1 and 243-3.

Physicians' Desk Reference, 54$^{th}$ Edition, 2000. pp. 1726-1727.

PDR 2000, Synalar/Lidex entries, pp. 1726-1727.

Katz M., et al. "Scholtz-Dumas psoriasis small plaque bioassay" Journal of Dermatological Treatment (2000) vol. 11, pp. 15-19.

Beger, et al. "Developing 13C NMR Quantitative Spectrometric Data-Activity Relationship (QSDAR) Models of Steroid binding to the Corticosteroid binding Globulin" Journal of Computer-Aided Molecular Design (2001) vol. 15, No. 7, pp. 659-669.

AHFS Drug Information, 2003, 84:06, pp. 3404, 3407, 3410-3411.

Hammer, et al. "Glucocorticoid Receptor Interactions with Glucocorticoids: Evaluation by Molecular Modeling and Functional Analysis of Glucocorticoid Receptor Mutants" Steroids (2003) vol. 68, No. 4, pp. 329-339.

Buchwald, et al. "Soft Glucocorticoid Design: Structural Elements and Physicochemical Parameters determining Receptor-Binding Affinity" Die Pharmazie (2004) vol. 59, pp. 396-404.

Bledsoe, et al. "Structure and Function of the Glucocorticoid Receptor Ligand Binding Domain" Vitamins and Hormones (2004) vol. 68, pp. 49-91.

Rhen, et al. "Antiinflammatory Action of Glucocorticoids—New Mechanisms for Old Drugs" The New England Journal of Medicine (2005) vol. 353, pp. 1711-1723.

Rosenkranz, G. "The Early Days of Syntex" (2005), pp. 10-12.

Zhou, et al. "The Human Glucocorticoid Receptor: One Gene, Multiple Proteins and Diverse Responses" Steroids (2005) vol. 70, pp. 407-417.

Megrab, et al., "Oestradiol permeation through human skin and silastic membrane: effects of propylene glycol and supersaturation," Journal of Controlled Release (1995), vol. 36, No. 3, pp. 277-294.

* cited by examiner

COMPOSITIONS AND METHODS FOR ENHANCING CORTICOSTEROID DELIVERY

CROSS REFERENCE TO RELATED APPLICATION

The present application is a continuation of U.S. application Ser. No. 10/825,977 filed Apr. 16, 2004, now abandoned, which is a continuation of U.S. application Ser. No. 10/037,360 filed Dec. 21, 2001, now U.S. Pat. No. 6,765,001.

FIELD OF THE INVENTION

Topical corticosteroids are useful for their anti-inflammatory, anti-pruritic and vasoconstrictive actions. Corticosteroids (or corticoids) are any steroids (lipids that contain a hydrogenated cyclopentoperhydrophenanthrene ring system) elaborated by the adrenal cortex (except sex hormones of adrenal origin) in response to the release of adrenocorticotrophin or adrenocorticotropic hormone by the pituitary gland, or to any synthetic equivalent, or to angiotensin II. Corticosteroids include but are not limited to alclometasone dipropionate, amcinonide, amcinafel, amcinafide, beclamethasone, betamethasone, betamethasone dipropionate, betamethasone valerate, clobetasone propionate, chloroprednisone, clocortelone, cortisol, cortisone, cortodoxone, difluorosone diacetate, descinolone, desonide, defluprednate, dihydroxycortisone, desoximetasone, dexamethasone, deflazacort, diflorasone diacetate, dichlorisone, esters of betamethasone, flucetonide, flucloronide, fluorocortisone, flumethasone, flunisolide, fluocinonide, fluocinolone acetonide, flucortolone, fluperolone, fluprednisolone, fluoroandrenolone a cetonide, fluocinolone acetonide, flurandrenolide, fluorametholone, fluticasone propionate, hydrocortisone, hydrocortisone butyrate, hydrocortisone valerate, hydrocortamate, medrysone, meprednisone, methylprednisone, methylprednisolone, mometasone furoate, paramethasone, prednisone, prednisolone, prednidone, triamcinolone acetonide, and triamcinolone.

Hydrocortisone was the first corticosteroid found to be topically effective. Other more potent glucocorticoids, which are a subset of corticosteroids that affect carbohydrate metabolism, inhibit corticotropin secretion, and possess pronounced anti-inflammatory activity, have since been developed. Currently, topical steroids are among the most frequently prescribed of all dermatological drug products.

It is believed that glucocorticoids exert their potent anti-inflammatory effects by inhibiting the formation of prostaglandins and other derivatives of the arachidonic acid pathway. It is known that glucocorticoids inhibit the release of phospholipase A2, the enzyme responsible for liberating arachidonic acid from cell membranes, thus inhibiting the arachidonic acid pathway. Currently, it is believed that glucocorticoids inhibit phospholipase A2, in cells by directly inducing phosphorylation of the enzyme.

Steroids are commonly divided into two classes, fluorinated and nonfluorinated. Fluorinated steroids have been chemically modified to increase potency. These modifications, such as halogenation and methylation, can result in improved activity within the target cell and in decreased breakdown to inactive metabolites. These modifications can also lead to more systemic side effects. However, modification of the chemical structure of the steroid is not the only way to increase potency.

The potency of topical steroid preparations is strongly correlated to their absorption through the skin. Treatment of the skin prior to application of the topical steroid may also affect the absorption of the compounds into the skin. Treatments with keratolytics or with fat solvents (such as acetone) disrupt the epidermal barrier and increase penetration. Hydrating the skin has also been shown to increase the penetration of the corticosteroids.

Once absorbed through the skin, topical corticosteroids are handled through pharmacokinetic pathways similar to systemically administered corticosteroids. The potencies of corticosteroids vary greatly and it is a challenge to increase the potency of any particular steroid.

BACKGROUND OF THE INVENTION

The clinical effectiveness of corticoids is related to four basic properties: vasoconstriction, antiproliferative effects, immunosuppression, and anti-inflammatory effects. Topical steroids cause the capillaries in the superficial dermis to constrict, thus reducing erythema. The ability of a given glucocorticoid agent to cause vasoconstriction usually correlates with its anti-inflammatory potency. Vasoconstrictor assays are used in the art and by the U.S. Food and Drug Administration for determining the potency of topical corticosteroid preparations. Topical glucocorticoid preparations have been divided in the field into seven classes based on potency based on double-blind clinical studies and vasoconstrictor assays. Class 1 includes the most potent, while class 7 contains the least potent.

The following glucocorticoid preparations were designated in Fitzpatrick, *Dermatology in General Medicine*, 5th edition, CD-ROM, 1999, Table 243-1, with the following classes.

TABLE 1

| Corticosteroid Preparation | Corticosteroid | Class | Source |
|---|---|---|---|
| Temovate ® Cream 0.05% | Clobetasone propionate | 1 | Glaxo Wellcome |
| Temovate ® ointment 0.05% | Clobetasone propionate | 1 | Glaxo Wellcome |
| Diprolene ® cream 0.05% | Betamethasone dipropionate | 1 | Schering Corp. |
| Diprolene ® ointment 0.05% | Betamethasone dipropionate | 1 | Schering Corp. |
| Psorcon ® ointment | Diflorasone diacetate | 1 | Dermik Laboratories, Inc. |
| Cyclocort ® ointment 0.1% | Amcinonide | 2 | Fujisawa |
| Diprolene ® cream AF 0.05% | Betamethasone dipropionate | 2 | Schering Corp. |
| Diprosone ® ointment 0.05% | Betamethasone dipropionate | 2 | Schering Corp. |

TABLE 1-continued

| Corticosteroid Preparation | Corticosteroid | Class | Source |
|---|---|---|---|
| Elocon ® ointment 0.1% | Mometasone furoate | 2 | Schering Corp. |
| Florone ® ointment 0.05% | Diflorasone diacetate | 2 | Dermik |
| Halog ® cream 0.1% | Halcinonide | 2 | Westwood-Squibb |
| Lidex ® gel 0.05% | Fluocinonide | 2 | Medicis Pharmaceuticals Corp. |
| Lidex ® cream 0.05% | Fluocinonide | 2 | Medicis Pharmaceuticals Corp. |
| Lidex ® ointment 0.05% | Fluocinonide | 2 | Medicis Pharmaceuticals Corp. |
| Maxiflor ® ointment 0.05% | Diflorasone diacetate | 2 | Allergan Herbert |
| Topicort ® cream 0.25% | Desoximetasone | 2 | Medicis Pharmaceuticals Corp. |
| Topicort ® gel 0.05% | Desoximetasone | 2 | Medicis Pharmaceuticals Corp. |
| Topicort ® ointment 0.25% | Desoximetasone | 2 | Medicis Pharmaceuticals Corp. |
| Aristocort A ® ointment 0.1% | Triamcinolone acetonide | 3 | Fujisawa |
| Cutivate ® ointment 0.005% | Fluticasone propionate | 3 | Glaxo Wellcome |
| Cyclocort ® cream 0.1% | Amcinonide | 3 | Fujisawa |
| Cyclocort ® Lotion 0.1% | Amcinonide | 3 | Fujisawa |
| Diprosone ® cream 0.05% | Betamethasone dipropionate | 3 | Schering Corp. |
| Florone ® cream 0.05% | Diflorasone diacetate | 3 | Dermik |
| Halog ® ointment 0.1% | Halcinonide | 3 | Westwood-Squibb |
| Lidex ® E cream 0.05% | Fluocinonide | 3 | Medicis Pharmaceutical Corp. |
| Maxiflor ® cream 0.05% | Diflorasone diacetate | 3 | Allergan Herbert |
| Valisone ® ointment 0.1% | Betamethasone valerate | 3 | Schering Corp. |
| Cordran ® ointment 0.05% | Flurandrenolide | 4 | Oclassen |
| Elocon ® cream 0.1% | Mometasone furoate | 4 | Schering Corp. |
| Kenalog ® cream 0.1% | Triamcinolone acetonide | 4 | Westwood-Squibb |
| Synalar ® ointment 0.025% | Fluocinolone acetonide | 4 | Medicis Pharmaceuticals Corp. |
| Westcort ® ointment 0.2% | Hydrocortisone valerate | 4 | Westwood-Squibb |
| Cordran ® cream 0.05% | Flurandrenolide | 5 | Oclassen |
| Cutivate ® cream 0.05% | Fluticasone propionate | 5 | Glaxo Wellcome |
| Diprosone ® lotion 0.05% | Betamethasone dipropionate | 5 | Schering Corp. |
| Kenalog ® lotion 0.1% | Triamcinolone acetonide | 5 | Westwood-Squibb |
| Locoid ® cream 0.1% | Hydrocortisone butyrate | 5 | Ferndale |
| Synalar ® cream 0.025% | Flucinolone acetonide | 5 | Medicis Pharmaceuticals Corp. |
| Valisone ® cream 0.1% | Betamethasone valerate | 5 | Schering Corp. |
| Westcort ® cream 0.2% | Hydrocortisone valerate | 5 | Westwood-Squibb |
| Aclovate ® cream 0.05% | Alclometasone dipropionate | 6 | Glaxo Wellcome |
| Aclovate ® ointment 0.05% | Alclometasone dipropionate | 6 | Glaxo Wellcome |
| Aristocort ® cream 0.1% | Triamcinolone acetonide | 6 | Fujisawa |
| Desowen ® cream 0.05% | Desonide | 6 | Galderma |
| Synalar ® solution 0.01% | Fluocinolone acetonide | 6 | Medicis Pharmaceuticals Corp. |
| Synalar ® cream 0.01% | Fluocinolone acetonide | 6 | Medicis Pharmaceuticals Corp. |
| Tridesilon ® cream 0.05% | Desonide | 6 | Miles |
| Valisone ® lotion 0.1% | Betamethasone valerate | 6 | Schering Corp. |
| Topicals with hydrocortisone dexamethasone, flumethasone, prednisolone, and methylprednisolone | | 7 | |

All percentages given are weight percentages unless otherwise noted.

Although there is no significant difference between potencies within Class 2, within Class 1 Temovate® cream or ointment is significantly more potent than Class 1 Diprolone® cream or ointment of Schering and Class 1 Psorcon® ointment of Dermik Laboratories, Inc.

Several factors such as the vehicle, the integrity of the epidermal barrier, and the use of occlusive dressings affect the percutaneous absorption and resulting potency of corticosteroids regardless of the intrinsic potency of the glucocorticosteroid (or glucocorticoid) molecule. Further, inflammation and/or other disease processes in the skin increase percutaneous absorption.

The vehicle in which the corticoid is incorporated may be as important as the corticoid molecule itself in determining the potency of a given formulation because the vehicle affects the amount of corticoid that is released in any given period of time, and its absorption. In many corticosteroid compositions, the vehicle is as much as 99% of the total composition. Very occlusive vehicles, such as ointments (water-insoluble mixtures of oil and petrolatum), increase the corticosteroid effect because they provide increased hydration of the stratum corneum and increase the skin's permeability. By covering the skin with an occlusive dressing such as plastic wrap, this effect c an be heightened as much as 100-fold. The solubility of the corticoid in the vehicle also affects penetration into the skin.

Creams, which are suspensions of oil in water, have also been used as vehicles for corticosteroids. The compositions of creams vary and are far less greasy than ointments but do not provide the same degree of hydration to the skin, and therefore may not have as high penetration as ointments. Lotions, which are suspensions of oil in water and are similar to creams, are vehicles which include agents to help solubilize the corticosteroids. Solutions have been used as vehicles and are water based with propylene glycol. Gels are solid components at room temperature but melt on the skin. Lotions, gels and solutions have less penetration than ointments.

Many vehicles for corticosteroids include propylene glycol for dissolving the corticosteroid in the vehicle. In general, compositions that contain higher amounts of propylene glycol tend to be more potent.

Vehicles are so important in the potency of corticosteroids that different formulations containing the same amount of the same corticosteroid often are in different potency classes. For example, commercially available preparations of 0.05% betamethasone dipropionate are classified as having Class 1, Class 2 or Class 3 potency, depending on their vehicles (as seen in Table 1).

SUMMARY OF THE INVENTION

The present invention comprises a novel vehicle which is safe for topical application, stable, and provides increased potency for corticosteroid preparations, especially fluorinated corticosteroids.

An embodiment of the present invention delivers the corticosteroid in a vehicle that comprises a corticosteroid, and (a) at least two penetration enhancers, including propylene glycol, dimethyl isosorbide or diisopropyl adipate, (b) solvents and/or emulsifiers for the corticosteroid and optionally the penetration enhancers and (c) optionally, non-solvent/emulsifier ingredients. The vehicle has a ratio of a:(a+b) that is greater than or equal to 0.70, preferably greater than or equal to 0.80 and most preferably greater than or equal to 0.90 or 0.95.

DETAILED DESCRIPTION OF THE PREFERRED EMBODIMENTS

The present invention enhances the potency of corticosteroid preparations with a vehicle comprising at least two penetration enhancers, including diisopropyl adipate, dimethyl isosorbide, propylene glycol, 1,2,6-hexanetriol, and benzyl alcohol. The corticosteroids with which this invention may be used include, but are not limited to, fluorinated corticosteroids.

Another embodiment of the present invention is a method for enhancing the potency of corticosteroids, preferably fluorinated corticosteroids. The corticosteroid is combined with two or more penetration enhancers (preferably propylene glycol and at least one other penetration enhancer), and one or more solvents and emulsifiers for the corticosteroid and optionally penetration enhancers, wherein the penetration enhancers are present in ratio to the total of the penetration enhancers, and solvents and emulsifiers of at least about 0.70, preferably at least 0.80 and most preferably 0.90 or 0.95. Optionally, one or more inactive ingredients may also be combined with the corticosteroid.

Another embodiment of the present invention is a method of delivering corticosteroids to skin, nails or hair, preferably mammalian skin, most preferably human, dog or cat skin. The corticosteroids are preferably fluorinated corticosteroids. The corticosteroid is combined with two or more penetration enhancers, and one or more solvents and emulsifiers for the corticosteroid, wherein the penetration enhancers are present in ratio to the total of the penetration enhancers, and solvents and emulsifiers of at least about 0.70, preferably at least 0.85 and most preferably 0.90 or 0.95. Optionally, one or more inactive ingredients may also be combined with the corticosteroid.

As indicated above, this invention is broadly applicable to corticosteroids in general, and fluorinated corticosteroids in particular, most preferably fluocinonide or fluocinolone acetonide. The following examples show its application to preparations of fluocinonide, a commonly used fluorinated corticosteroid. Fluocinonide is a corticosteroid which is the 21-acetate ester of fluocinolone acetonide with the chemical name pregna-1,4-diene-3,20-dione,21-(acetyloxy)-6,9-difluoro-11-hydroxy-16, 17-[(1-methylethylidene)bis(oxy)]-, (6α,11β,16α)-. Compositions containing 0.05% (all percentages are weight percentages) fluocinonide are commonly classified as Class 2.

EXAMPLE 1

Experiments were conducted with embodiments of the present invention and several control compositions. Compositions were p prepared and the investigator was blinded with respect to the compositions. Thirty-six healthy volunteers were enrolled for two-day trials. On day 1, a single application of approximately 10 milligrams of at least eight compositions was made to 1 $cm^2$ sites on the lower aspect of each volunteer's forearms in accordance with a computer generated randomization code. After applying the compositions, the sites were protected using a raised perforated guard. The guard was secured to the arm with a non-occlusive tape and the subjects were scheduled to return the following day after being instructed to keep the sites dry.

After approximately 16 hours of contact with the skin, the protective guards were removed and the compositions were removed from the test sites by gently washing with mild soap and water. Skin vasoconstrictor evaluations were performed on a four point scale (0-3) at approximately 18 hours after application.

Scores for skin vasoconstriction were summed for each composition (each composition was applied to thirty-six volunteers and those thirty-six scores were summed). For each composition tested, the ratio of penetration enhancers (a) to the sum of penetration enhancers, and solvents and emulsifiers (a+b) was calculated (a:(a+b)). All of the compositions comprise 0.10% fluocinonide.

TABLE 2

| | Range of a:(a + b) | | | | | |
|---|---|---|---|---|---|---|
| | 1-0.95 | 0.94-0.90 | 0.89-0.80 | 0.79-0.70 | 0.69-0.60 | 0.59-0.50 |
| Average of Summed Vasoconstrictor Scores | 93 | 85 | 71 | 72 | 62 | 58 |

* means there were no samples with the range of 0.59 to 0.55.

As seen in the above table, the average vasoconstrictor scores are significantly lower for ranges of a :(a+b)<0.70. The corticosteroid preparations with average vasoconstrictor scores of 58 and 62 are significantly less potent than those preparations with average vasoconstrictor scores of 72 and higher. Scores of 62 and 58 are not significantly different. This magnitude of increase in vasoconstrictor scores is typical of an increase in class.

Several control compositions (with 0.10% fluocinonide and no penetration enhancers, as defined below, were included) were also tested for their vasoconstrictor scores in the same manner. Therefore, the ratios of a:(a+b) are zero. The vasoconstrictor scores are 60.00 and 59.00, which are significantly lower than the present invention's embodiments' vasoconstrictor scores.

Additionally, several other control compositions were tested for their vasoconstrictor scores ("vasoscores"). These compositions comprised 0.10% fluocinonide, and no diisoproyl adipate, propylene glycol or dimethyl isosorbide. Their vasoscores were 49.00, 47.00 and 44.00.

The experiments also included several Class 1 compositions as comparison points. Psorcon® ointment by Dermik Laboratories, Inc. of Collegeville, Pa. with 0.05% diflorasone diacetate had a vasoscore of 101. Ultravate® ointment by Westwood-Squibb of Evansville, Ind. with 0.05% halobetasol propionate had a vasoscore of 97, while Ultravate® cream by Westwood-Squibb with 0.05% halobetasol propionate had a vasoscore of 92.

In the ratio of (a):(a+b), penetration enhancers include at least two of: propylene glycol, diisopropyl adipate, dimethyl isosorbide, 1,2,6 hexanetriol, and benzyl alcohol (collectively referred to as "a"). The solvents and emulsifiers for the corticosteroid include one or more of dehydrated alcohol, alcohol (95% v/v) USP, 3-Cyclohexene-1-Methanol, ∝4-Dimethyl-a-(4-Methyl-3-Pentenyl)-, Steareth-2, Steareth-21, citric acid, CPE-215, diisopropanolamine (1:9), DIPA/PG (1:9), ethoxydiglycol, Potassium hydroxide (10%), PEG-40 Stearate, PEG-7000, Polysorbate 60, potassium hydroxide (1%), propylene carbonate USP, propylethylene glycol 4, oleyl alcohol, sodium lauryl sulfate, sorbitan monostearate, sorbitan stearate, and 1,2,3-Propanetriol Ester (collectively referred to as "b").

The compositions optionally comprise non-solvent/emulsifier ingredients, such as Glyceryl Stearate (and) PEG-100 Stearate, carbopol 980, cyclomethicone NF, glyceryl monostearate, hydroxyethyl cellulose, hydroxypropyl cellulose, isopropyl myristate, methyl paraben NF, mineral oil, oleic acid NF, PEG-100 Stearate, petrolatum, propyl paraben NF, purified water, stearyl alcohol, white petrolatum, and white wax.

The combination of penetration enhancers used in the invention have a remarkable and unexpected result. Compounds using similar concentrations of a single penetration enhancer (e.g. propylene glycol as the sole penetration enhancer with 0.10% fluocinonide yielded vasoscores of 72.00, and 50.00, depending on the solvents, emulsifiers and non-solvent/emulsifier ingredients used) do not have similarly high vaso scores. Compositions with the combination of penetration enhancers and formula scores of less than 0.65 also have low vaso scores. Therefore the invention results in an unexpected increase in potency of the fluocinonide.

EXAMPLE 2

One embodiment of the present invention is detailed in the chart below.

TABLE 3

| Component | % w/w | % w/w |
|---|---|---|
| Fluocinonide Micronized, USP | 0.1 | 0.1 |
| Propylene Glycol, USP | 70.0 | 74.9 |
| Dimethyl isosorbide | 15.0 | |
| Diisopropyl Adipate | | 3.0 |
| Isopropyl Myristate, NF | | 5.0 |
| 1,2,6 Trihydroxyhexane | | 2.5 |
| Carbopol 980 | 1.2 | 1.0 |
| Diisopropanolamine 85%: propylene glycol (1:9) | 1.2 | 1.0 |
| Citric Acid, USP | 0.01 | 0.01 |
| Purified Water, USP | 2.49 | 2.49 |
| Glyceryl monostearate | 2.5 | 2.5 |
| Glyceryl monostearate & PEG stearate | 7.5 | 7.5 |

EXAMPLE 3

Another embodiment of the present invention is detailed in the chart below.

TABLE 4

| Component | % w/w | % w/w |
|---|---|---|
| Fluocinonide Micronized, USP | 0.1 | 0.1 |
| Propylene Glycol, USP | 66.8 | 69.9 |
| Dimethyl isosorbide | 5.0 | |
| Diisopropyl Adipate | | 2.0 |
| Isopropyl Myristate, NF | 5.0 | 5.0 |
| Carbopol 980 | 0.5 | 0.5 |
| Diisopropanolamine 85%: propylene glycol (1:9) | 0.5 | 0.5 |
| White Petrolatum, USP | 5.0 | 5.0 |

TABLE 4-continued

| Component | % w/w | % w/w |
|---|---|---|
| Glyceryl monostearate | 6.0 | 6.0 |
| PEG 100 stearate | 6.0 | 6.0 |
| Stearyl alcohol, NF | 5.0 | 5.0 |
| Sodium Lauryl Sulfate, NF | 0.1 | |

It is to be understood that while the invention has been described in conjunction with the detailed description thereof, that the foregoing description is intended to illustrate and not limit the scope of the invention, which is defined by the scope of the appended claims. Other aspects, advantages, and modifications are evident from a review of the following claims.

What is claimed is:

1. A composition consisting essentially of
One or more corticosteroids;
Two or more penetration enhancers selected from the group consisting of diisopropyl adipate, dimethyl isosorbide, propylene glycol, 1,2,6-hexanetriol, and benzyl alcohol; and
One or more of the group consisting of solvents and emulsifiers, wherein the solvents and emulsifiers are selected from the group consisting of dehydrated alcohol, alcohol (95% v/v) USP, 3-Cyclohexene-1-Methanol, .α.4-Dimethyl-a-(4-Methyl-3-Pentenyl)-, Steareth-2, Steareth-21, citric acid, CPE-215, diisopropanolamine (1:9), DIPA/PG (1:9), ethoxydiglycol, Potassium hydroxide (10%), PEG40 Stearate, PEG-7000, Polysorbate 60, potassium hydroxide (1%), propylene carbonate USP, propylethylene glycol4, oleyl alcohol, sodium lauryl sulfate, sorbitan monostearate, sorbitan stearate, and 1,2,3-Propanetriol Ester, and wherein the penetration enhancers are present in a ratio to a total of the penetration enhancers, and solvents and emulsifiers of at least about 0.9.

2. The composition of claim 1 wherein the corticosteroid comprises a fluorinated corticosteroid.

3. The composition of claim 1 wherein the corticosteroid comprises fluocinonide.

4. The composition of claim 1 wherein the corticosteroid comprises fluocinolone acetonide.

5. The composition of claim 1, 2, 3 or 4 wherein the corticosteroid is present at about 0.10%.

6. The composition of claim 1, 2, 3 or 4 wherein the corticosteroid is present at least about 0.50%.

7. The composition of claim 1, 2, 3 or 4 wherein the corticosteroid is present at least about 0.25%.

8. The composition of claim 1, 2, 3 or 4 wherein one penetration enhancer comprises propylene glycol.

9. The composition of claim 1 wherein the ratio is at least about 0.95.

10. The composition of claim 1 further comprising one or more non-solvent/emulsifier ingredients.

11. The composition of claim 10 wherein the non-solvent/emulsifier ingredients comprise one or more of the group consisting of Glyceryl Stearate (and) PEG-100 Stearate, carbopol 980, cyclomethicone NF, glyceryl monostearate, hydroxyethyl cellulose, hydroxypropyl cellulose, isopropyl myristate, methyl paraben NF, mineral oil, oleic acid NF, PEG-100 Stearate, petrolatum, propyl paraben NF, purified water, stearyl alcohol, white petrolatum, and white wax.

12. The composition of claim 1 wherein the solvents and emulsifiers are present at about 4-5%.

13. The composition of claim 10 wherein the non-solvent/emulsifier ingredients are present at about 11% to about 53%.

14. The composition of claim 10 wherein the non-solvent/emulsifier ingredients are present at about 11% to about 27%.

15. A composition consisting essentially of
one or more corticosteroids;
two or more penetration enhancers selected from the group consisting of diisopropyl adipate, dimethyl isosorbide, propylene glycol, 1,2,6-hexanetriol, and benzyl alcohol;
one or more solvents/emulsifiers, wherein the solvents and emulsifiers are selected from the group consisting of dehydrated alcohol, alcohol (95% v/v) USP, 3-Cyclohexene-1-Methanol, .α.4-Dimethyl-a-(4-Methyl-3-Pentenyl)-, Steareth-2, Steareth-21, citric acid, CPE-215, diisopropanolamine (1:9), DIPA/PG (1:9), ethoxydiglycol, Potassium hydroxide (10%), PEG40 Stearate, PEG-7000, Polysorbate 60, potassium hydroxide (1%), propylene carbonate USP, propylethylene glycol 4, oleyl alcohol, sodium lauryl sulfate, sorbitan monostearate, sorbitan stearate, and 1,2,3-Propanetriol Ester; and
one or more non-solvent/emulsifier ingredients, wherein the non-solvent/emulsifier ingredients comprise one or more of the group consisting of Glyceryl Stearate (and) PEG-100 Stearate, carbopol 980, cyclomethicone NF, glyceryl monostearate, hydroxyethyl cellulose, hydroxypropyl cellulose, isopropyl myristate, methyl paraben NF, mineral oil, oleic acid NF, PEG-100 Stearate, petrolatum, propyl paraben NF, purified water, stearyl alcohol, white petrolatum, and white wax, and wherein the one or more non-solvent/emulsifier ingredients include purified water, and
wherein the penetration enhancers are present in a ratio to a total of the penetration enhancers, and solvents/emulsifiers of at least about 0.90.

16. The composition of claim 15 wherein the corticosteroid comprises a fluorinated corticosteroid.

17. The composition of claim 15 wherein the corticosteroid comprises fluocinonide.

18. The composition of claim 15 wherein the corticosteroid comprises fluocinolone acetonide.

19. The composition of claim 15, 16, 17 or 18 wherein the corticosteroid is present at about 0.10%.

20. The composition of claim 15, 16, 17 or 18 wherein the corticosteroid is present at least about 0.50%.

21. The composition of claim 15, 16, 17 or 18 wherein the corticosteroid is present at least about 0.25%.

22. The composition of claim 15, 16, 17 or 18 wherein one penetration enhancer comprises propylene glycol.

23. The composition of claim 15 wherein the ratio is at least about 0.95.

24. The composition of claim 15 wherein the solvents and emulsifiers are present at about 4-5%.

25. The composition of claim 15 wherein the non-solvent/emulsifier ingredients are present at about 11% to about 53%.

26. The composition of claim 15 wherein the non-solvent/emulsifier ingredients are present at about 11% to about 27%.

27. A composition consisting essentially of
one or more corticosteroids;
two or more penetration enhancers, wherein the first penetration enhancer is propylene glycol and the second penetration enhancer is selected from the group consisting of diisopropyl adipate, dimethyl isosorbide, 1,2,6 hexanetriol, and benzyl alcohol;
one or more solvents/emulsifiers, wherein the solvents and emulsifiers are selected from the group consisting of dehydrated alcohol, alcohol (95% v/v) USP, 3-Cyclohexene-1-Methanol, .α.4-Dimethyl-a-(4-Methyl-3-Pentenyl)-, Steareth-2, Steareth-21, citric acid, CPE-215, diisopropanolamine (1:9), DIPA/PG (1:9), ethoxydiglycol, Potassium hydroxide (10%), PEG40 Stearate, PEG-7000, Polysorbate 60, potassium hydroxide (1%), propylene carbonate USP, propylethylene glycol 4, oleyl alcohol, sodium lauryl sulfate, sorbitan monostearate, sorbitan stearate, and 1,2,3-Propanetriol Ester; and one or more non-solvent/emulsifier ingredients, wherein the non-solvent/emulsifier ingredients comprise one or more of the group consisting of Glyceryl Stearate (and) PEG-100Stearate, carbopol 980, cyclomethicone NF, glyceryl monostearate, hydroxyethyl cellulose, hydroxypropyl cellulose, isopropyl myristate, methyl paraben NF, mineral oil, oleic acid NF, PEG-100 Stearate, petrolatum, propyl paraben NF, purified water, stearyl alcohol, white petrolatum, and white wax, and wherein the one or more non-solvent/emulsifier ingredients include purified water and wherein the penetration enhancers are present in a ratio to a total of the penetration enhancers, and solvents/emulsifiers of at least about 0.90 wherein the propylene glycol is at least 66.8% of the composition.

28. The composition of claim 27 wherein the propylene glycol is between 66.8% and 74.9% of the composition.

29. A composition comprising
One or more corticosteroids;
Two or more penetration enhancers wherein the first penetration enhancer is dimethyl isosorbide and the second penetration enhancer is selected from the group consisting of diisopropyl adipate, propylene glycol, 1,2,6-hexanetriol, and benzyl alcohol; and
One or more of the group consisting of solvents and emulsifiers, wherein the solvents and emulsifiers are selected from the group consisting of dehydrated alcohol, alcohol (95% v/v) USP, 3-Cyclohexene-1-Methanol, .α.4-Dimethyl-a-(4-Methyl-3-Pentenyl)-, Steareth-2, Steareth-21, citric acid, CPE-215, diisopropanolamine (1:9), DIPA/PG (1:9), ethoxydiglycol, Potassium hydroxide (10%), PEG40 Stearate, PEG-7000, Polysorbate 60, potassium hydroxide (1%), propylene carbonate USP, propylethylene glycol 4, oleyl alcohol, sodium lauryl sulfate, sorbitan monostearate, sorbitan stearate, and 1,2,3-Propanetriol Ester, wherein the penetration enhancers are present in a ratio to a total of the penetration enhancers, and solvents and emulsifiers of at least about 0.90.

30. The composition of claim 29 wherein the corticosteroid comprises a fluorinated corticosteroid.

31. The composition of claim 29 wherein the corticosteroid comprises fluocinonide.

32. The composition of claim 29 wherein the corticosteroid comprises fluocinolone acetonide.

33. The composition of claim 29, 30, 31, or 32 wherein the corticosteroid is present at about 0.10%.

34. The composition of claim 29, 30, 31, or 32 wherein the corticosteroid is present at at least about 0.50%.

35. The composition of claim 29, 30, 31, or 32 wherein the corticosteroid is present at at least about 0.25%.

36. The composition of claim 29, 30, 31, or 32 wherein the second penetration enhancer comprises propylene glycol.

37. The composition of claim 29 wherein the ratio is at least about 0.95.

38. The composition of claim 29 further comprising one or more non-solvent/emulsifier ingredients.

39. The composition of claim 38 wherein the non-solvent/emulsifier ingredients comprise one or more of the group consisting of Glyceryl Stearate (and) PEG-100 Stearate, carbopol 980, cyclomethicone NF, glyceryl monostearate, hydroxyethyl cellulose, hydroxypropyl cellulose, isopropyl myristate, methyl paraben NF, mineral oil, oleic acid NF, PEG-100 Stearate, petrolatum, propyl paraben NF, purified water, stearyl alcohol, white petrolatum, and white wax.

40. The composition of claim 29 wherein the solvents and emulsifiers are present at about 4-5%.

41. The composition of claim 38 wherein the non-solvent/emulsifier ingredients are present at about 11% to about 53%.

42. The composition of claim 38 wherein the non-solvent/emulsifier ingredients are present at about 11% to about 27%.

43. A composition consisting essentially of
one or more corticosteroids;
two or more penetration enhancers wherein the first penetration enhancer is dimethyl isosorbide and the second penetration enhancer is selected from the group consisting of diisopropyl adipate, propylene glycol, 1,2,6-hexanetriol, and benzyl alcohol;
one or more solvents/emulsifiers, wherein the solvents and emulsifiers are selected from the group consisting of dehydrated alcohol, alcohol (95% v/v) USP, 3-Cyclohexene-1-Methanol, .α.4-Dimethyl-a-(4-Methyl-3-Pentenyl)-, Steareth-2, Steareth-21, citric acid, CPE-215, diisopropanolamine (1:9), DIPA/PG (1:9), ethoxydiglycol, Potassium hydroxide (10%), PEG40 Stearate, PEG-7000, Polysorbate 60, potassium hydroxide (1%), propylene carbonate USP, propylethylene glycol 4, oleyl alcohol, sodium lauryl sulfate, sorbitan monostearate, sorbitan stearate, and 1,2,3-Propanetriol Ester; and
one or more non-solvent/emulsifier ingredients, wherein the non-solvent/emulsifier ingredients comprise one or more of the group consisting of Glyceryl Stearate (and) PEG-100 Stearate, carbopol 980, cyclomethicone NF, glyceryl monostearate, hydroxyethyl cellulose, hydroxypropyl cellulose, isopropyl myristate, methyl paraben NF, mineral oil, oleic acid NF, PEG-100 Stearate, petrolatum, propyl paraben NF, purified water, stearyl alcohol, white petrolatum, and white wax, and wherein the one or more non-solvent/emulsifier ingredients include purified water, and
wherein the penetration enhancers are present in a ratio to a total of the penetration enhancers, and solvents/emulsifiers of at least about 0.90.

44. The composition of claim 43 wherein the corticosteroid comprises a fluorinated corticosteroid.

45. The composition of claim 43 wherein the corticosteroid comprises fluocinonide.

46. The composition of claim 43 wherein the corticosteroid comprises fluocinolone acetonide.

47. The composition of claim 43, 44, 45, or 46 wherein the corticosteroid is present at about 0.10%.

48. The composition of claim 43, 44, 45, or 46 wherein the corticosteroid is present at at least about 0.50%.

49. The composition of claim 43, 44, 45, or 46 wherein the corticosteroid is present at at least about 0.25%.

50. The composition of claim 43, 44, 45, or 46 wherein the second penetration enhancer comprises propylene glycol.

51. The composition of claim 43 wherein the ratio is at least about 0.95.

52. The composition of claim 43 wherein the solvents and emulsifiers are present at about 4-5%.

53. The composition of claim 43 wherein the non-solvent/emulsifier ingredients are present at about 11% to about 53%.

54. The composition of claim 43 wherein the non-solvent/emulsifier ingredients are present at about 11% to about 27%.

55. The composition of claim 50 wherein the propylene glycol is at least 66.8% of the composition.

56. The composition of claim 50 wherein the propylene glycol is between 66.8% and 74.9% of the composition.

* * * * *